United States Patent [19]

Swett et al.

[11] 4,065,066

[45] Dec. 27, 1977

[54] CABLE HANDLING

[75] Inventors: Alan M. Swett, Milton; Roderick D. Swift, Belmont, both of Mass.

[73] Assignee: The United States of America as represented by the Secretary of the Department of Health, Education and Welfare, Washington, D.C.

[21] Appl. No.: 728,312

[22] Filed: Sept. 30, 1976

[51] Int. Cl.$^2$ .......................................... B65H 51/20
[52] U.S. Cl. ............................ 242/47.12; 191/12.2 R; 242/54 R
[58] Field of Search ............... 242/54 R, 47.12, 47.01; 191/12.2 R

[56] References Cited

U.S. PATENT DOCUMENTS

| | | | |
|---|---|---|---|
| 2,605,977 | 8/1952 | Gleason | 242/54 R |
| 3,120,355 | 2/1964 | Bowman | 242/47.12 |

Primary Examiner—George F. Mautz

Attorney, Agent, or Firm—Charles Hieken

[57] ABSTRACT

A cable handling mechanism for an X-ray tomographic scanner having a rotor assembly for making a scan of about two revolutions and then rewinding to an initial position includes two axially displaced drums. One drum is attached to the rotor housing and rotates with it; the other is fixed to the stationary structure. A pulley carrier between the two drums is rotatable about the same axis and carries large and small idler pulleys. At one extreme end position one or more individual cables inside a loose-fitting flexible tube are wound around the rotating drum for two turns, around the large idler pulley and in the opposite direction around the fixed drum for a single turn, and a control cable is attached to the rotating drum wound in a direction opposite to that of the flexible tube but for only one turn, around the small idler pulley and in the opposite direction on the fixed drum for two turns to which the other end of the control cable is attached.

6 Claims, 4 Drawing Figures

![4,065,066]

CABLE HANDLING

The invention described herein was made in the course of or under a contract with the U.S. Department of Health, Education, and Welfare.

BACKGROUND OF THE INVENTION

The present invention relates in general to cable handling and more particularly concerns novel apparatus and techniques for handling cables interconnecting rotating and fixed components in an X-ray scanner in a manner that facilitates scanning back and forth many times while always keeping the interconnecting cables neatly dressed and free from damaging mechanical strains with a reliably operating mechanical structure relatively free from complexity and relatively easy and inexpensive to assemble and maintain.

A typical computer tomography system for obtaining X-ray cross section images of a patient includes a rotor assembly carrying an X-ray tube and other electromechanical devices. Exchanging electrical signals between fixed and rotating assemblies presents a problem because the moving X-ray tube requires high d-c potentials at significant current levels, and signals produced on the rotor assembly for processing by fixed components may be at relatively low levels. The use of relatively rotating contacts, such as brushes and slip rings, presents problems because of the potential for arcing at the high potentials and noise being introduced in low level signal paths. While these problems are overcome by using direct connections through cables, there are other problems in connection with properly dressing the cables during relative movement between the members.

Accordingly, it is an important object of the invention to provide an improved cable handling mechanism for use with an X-ray tomographic scanner.

It is another object of the invention to achieve the preceding object while overcoming one or more of the problems set forth above.

It is a further object of the invention to achieve one or more of the preceding objects with a structure that is relatively easy and inexpensive to assemble and maintain.

It is a further object of the invention to achieve one or more of the preceding objects with a mechanically compact assembly that adds only slightly to the weight and volume of the scanner and may be conveniently accommodated.

SUMMARY OF THE INVENTION

According to the invention, there are first and second drum means axially displaced and relatively rotatable about a common axis separated by pulley carrier means relatively rotatable with respect to both drum means about the same axis. The pulley carrier means carries first and second pulley means of different diameter for guiding first and second cable means about first and second arcuate paths of different length about first and second axes respectively generally perpendicular to the surface of said pulley carrier means. First and second points of said first cable means are fixed to said first and second drums respectively and arranged so that its standing part between these fixed points travels over said first arcuate path upon relative rotation between said first and second drum means and said pulley carrier means. Similarly, first and second points of said second cable means are connected to said first and second drum means respectively with its standing part between these fixed points arranged for being guided by said second pulley means along said second arcuate path with the first and second cable means being wrapped around said first and second drum means in opposite directions so that as one cable winds around a respective drum means, the other unwinds, and vice versa. In a specific form of the invention for allowing a peak relative angular displacement between the first and second drums of substantially two revolutions (720°), the diameter of the second pulley means is substantially four times that of the first pulley means. At one extreme end position the first cable means is wrapped twice around the second drum means and once around the first drum means, and the second cable means is wrapped twice around the first drum means and once around the second drum means so that the relative angular velocity and displacement between the pulley carrier means is half that between the first and second drum means. That is to say, when the first and second drum means move relatively two revolutions, the pulley carrier means moves one revolution relative to each drum means. The first cable means may function as a control cable and the second cable means may comprise the signal and power cables, preferably assembled inside a loose-fitting flexible tube.

Numerous other features, objects and advantages of the invention will become apparent from the following specification when read in connection with the accompanying drawing in which:

DETAILED DESCRIPTION OF PREFERRED EMBODIMENTS

Figure 1:
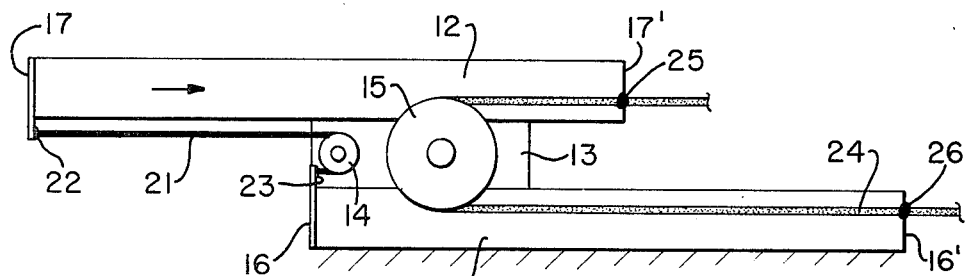
FIGS. 1-3 are diagrammatic representations of the invention with the drums unwound showing the relative positions among drums, pulley carrier and cables for one extreme end relative position, a position midway between the extreme end positions and the other extreme end position, respectively.
Figure 2:
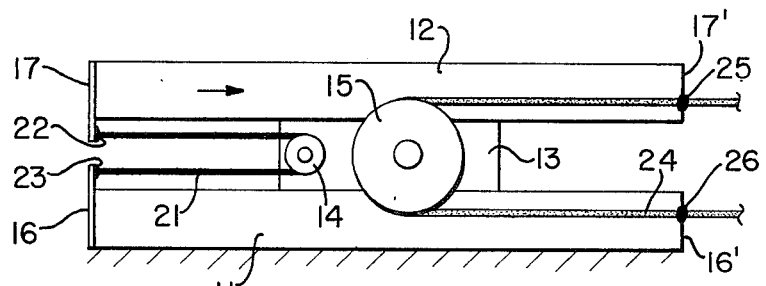
Figure 3:
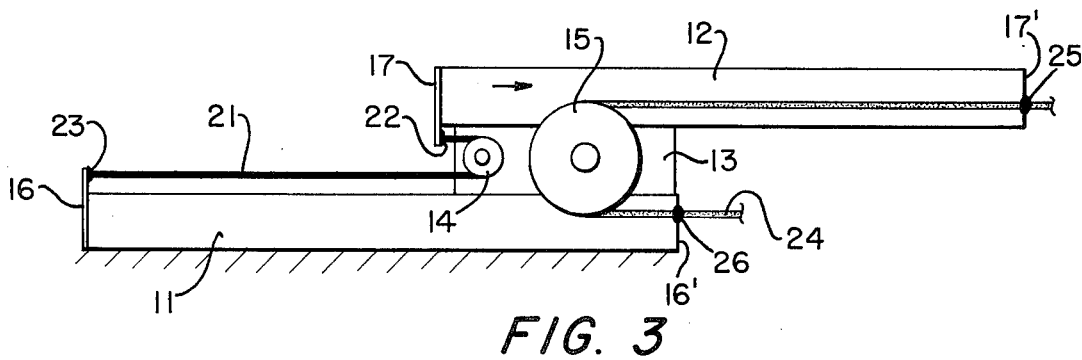

With reference now to the drawing, and more particularly FIGS. 1-3 thereof, there are shown diagrammatic representations of an embodiment of the invention with the drums unrolled to best illustrate the principles of the invention with the drums in one extreme end relative position, a position midway between the extreme end positions and the other extreme end position, respectively. The assembly includes a fixed drum 11 and a rotatable drum 12 separated by a pulley carrier 13 with a small idler pulley 14 and a large idler pulley 15. Since drums 11 and 12 are shown unrolled to better illustrate the principles of the invention, it will be understood that lines 16 and 16' of drum 11 and 17 and 17' of drum 12 coincide. A first or control cable 21 is connected at one point 22 to rotating drum 17 and at another point 23 to fixed drum 11 with its standing part therebetween being guided over a first arcuate path by small pulley 14. A second or electrical cable 24, typically comprising flexible cables for delivering filament and anode potential to an x-ray tube and cables for delivering other signals from the rotor assembly to the fixed assembly in a loose-fitting flexible tube, is connected at one point 25 to drum 12 and another point 26 to drum 11. Pulley carrier 13 separates drums 11 and 12 and is free to rotate about the axis common to drums 11 and 12 and pulley carrier 13.

The details of the specific means for mounting the drums, pulley carrier and pulleys are well-known in the art, not a part of the invention and omitted here to avoid obscuring the principles of the invention. Details of specific connections to components on the rotor assembly and fixed components are also omitted for the same reason.

Having described the physical arrangement of the invention, the principles of operation will now be described. FIG. 1 shows the system components of the invention with drum 12 at an extreme clockwise end position as viewed from the top of the assembly. In that position almost three turns of control cable 21 are wrapped clockwise about drum 12, and less than one turn is wrapped counterclockwise about drum 11. Less than one turn of electrical cable 24 is wrapped counterclockwise about drum 12 and almost three turns are wrapped clockwise about drum 11.

As drum 12 rotates counterclockwise one revolution, the assembly assumes the relative position shown in FIG. 2 with one turn wound upon and unwound from drums 12 and 11, respectively, of cable 24 and drums 11 and 12, respectively, of cable 26, and pulley carrier 13 advanced half a revolution counterclockwise about the common axis. This relative position is shown in FIG. 2.

As drum 12 rotates counterclockwise another revolution to the other extreme end position shown in FIG. 3, control cable 21 has unwound from drum 12 so that a turn remains there while winding an additional turn on drum 11 so that there are then two turns of cable 21 on drum 11 wound counterclockwise from point 23. Electrical cable 24 has then two turns wound clockwise about drum 12 from end 25 and only one turn on drum 11 would clockwise from end 26. Pulley carrier 13 has been advanced one revolution counterclockwise about the common axis. Control cable 21 functions to maintain tension in the system and to pull pulley carrier 13 in the clockwise direction when returning the drums to the initial extreme clockwise end position of FIG. 1.

For the specific system just described, the diameter of large pulley 15 is substantially four times that of small pulley 14 with the diameter of drums 11 and 12 being substantially the same. It is within the principles of the invention to chose other ratios of pulley diameters advantageous for specific applications.

Figure 4:
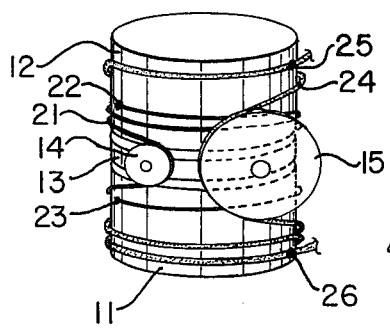
FIG. 4 is a simplified pictorial representation of the invention.

Referring to FIG. 4, there is shown a simplified pictorial representation of the invention with drums 11 and 12 and pulley carrier 13 shown in substantially the relative position of FIG. 2. Large and small pulleys 14 and 15 are of diameter greater than the width of pulley carrier 13 and function to guide cable 24 so that it resides on the portions of drums 11 and 12 furthest from pulley carrier 13 while cable 21 is stored on the portions of drum 11 and 12 near pulley carrier 13. Drum 12 is typically in fixed relationship with the rotor assembly of an X-ray tomographic scanner and cable 24 includes high voltage cables for connection to the X-ray tube carried by the rotor and one or more signal cables connected to electromechanical devices on the rotor assembly. The other end of cable 24 is connected to the high voltage power supply and amplifiers or other circuits associated with the fixed assembly. While a specific embodiment of the invention is used in a tomographic X-ray scanner to control the winding and unwinding of about 25 feet of cable, the invention is also useful where it is desired to exchange electrical energy or fluids between relatively rotating members, such as a rotating antenna for exchanging energy between the rotating antenna and a receiver and/or transmitter. Furthermore, while the exemplary embodiment uses only one of the two cables for exchanging electrical energy between the relatively rotating assemblies, it is within the principles of the invention to use either or both cables for exchanging electrical energy or fluids. It is also within the principles of the invention to use drums of different size and different orientation.

There has been described novel apparatus and techniques for dressing cables interconnecting a rotor assembly with stationary equipment with negligible mechanical strain on the cables in a manner that facilitates winding and unwinding over many cycles reliably with a compact mechanical package that is relatively easy and inexpensive to install and maintain. It is evident that those skilled in the art may now make numerous uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Cable handling apparatus comprising,
   first and second drum means axially displaced along and relatively rotatable about a common axis for carrying flexible cables thereon,
   pulley carrier means separating said first and second drum means and relatively rotatable about said common axis with respect to said first and second drum means for carrying pulley means,
   first and second pulley means mounted on said pulley carrier means for guiding flexible cables along first and second arcuate paths respectively of different lengths so that said pulley carrier means moves about said common axis as said pulleys guide cables over said arcuate paths,
   a first flexible cable having first and second points secured to said first and second drum means respectively and a standing part therebetween guidable over said first arcuate path by said first pulley means,
   and a second flexible cable having first and second points connected to said first and second drum means respectively and a standing part therebetween guidable over said second arcuate path by said second pulley means.

2. Cable handling apparatus in accordance with claim 1 wherein said first and second arcuate paths are angularly spaced about said common axis with the arcuate paths opening in opposite directions so that upon relative angular displacement between said first and second drums said first cable unwinds from one of said drums and winds on the other while said second cable unwinds on said one drum and winds on said other.

3. Cable handling apparatus in accordance with claim 2 wherein said first and second cables are wound in opposite sense about said first and second drums.

4. Cable handling apparatus in accordance with claim 3 and further comprising means for winding said first cable on near portions of said first and second drum means adjacent to said pulley carrier means and means for winding said second cable upon far portions of said first and second drum means spaced from said pulley carrier means by said near portions.

5. A method of cable handling which method includes the steps of,
rotating a first drum to which points on first and second cables are connected in a first sense to wind the first cable upon and unwind the second cable from said first drum while simultaneously unwinding the first cable from and winding the second cable upon a second stationary drum, and rotating said first drum in a second sense opposite said first sense to unwind the first cable from and wind the second cable upon said first drum while winding the first cable upon and unwinding the second cable from said second drum.

6. A method of cable handling in accordance with claim 5 and further including the step of winding said first and second cables in opposite directions about each of said drums.

* * * * *